(12) United States Patent
Restelli et al.

(10) Patent No.: US 6,319,234 B1
(45) Date of Patent: Nov. 20, 2001

(54) DISPOSABLE SAFETY SYRINGE

(76) Inventors: Sergio Restelli, Via Giacinta Pezzana, 9, Rome I-00197; Nardino Righi, Viale Padova, 314, Milan I-20132, both of (IT)

(*) Notice: Subject to any disclaimer, the term of this patent is extended or adjusted under 35 U.S.C. 154(b) by 0 days.

(21) Appl. No.: 09/367,319
(22) PCT Filed: Feb. 9, 1998
(86) PCT No.: PCT/EP98/00692
 § 371 Date: Sep. 8, 1999
 § 102(e) Date: Sep. 8, 1999
(87) PCT Pub. No.: WO98/35714
 PCT Pub. Date: Aug. 20, 1998
(51) Int. Cl.$^7$ ........................................ A61M 5/32
(52) U.S. Cl. ............................. 604/198; 604/110
(58) Field of Search .................... 604/181, 192, 604/194, 198, 110, 158, 164.01, 164.08, 187, 197

(56) References Cited

U.S. PATENT DOCUMENTS

| | | | |
|---|---|---|---|
| 4,850,968 | * 7/1989 | Romano | 604/110 |
| 4,957,490 | * 9/1990 | Byrne et al. | 604/197 |
| 5,163,918 | * 11/1992 | Righi et al. | 604/198 |
| 5,267,976 | * 12/1993 | Guerineau et al. | 604/198 |
| 5,562,624 | * 10/1996 | Righi et al. | 604/110 |
| 5,562,626 | * 10/1996 | Sanpietro | 604/110 |

* cited by examiner

Primary Examiner—Sharon Kennedy
Assistant Examiner—Catherine Serke
(74) Attorney, Agent, or Firm—James Creighton Wray; Meera P. Narasimhan

(57) ABSTRACT

The syringe is provided with a needle-covering sleeve (14), which is slidably fitted on the syringe barrel (1) and is held in its retracted rest position by means of retaining tongues (10), which hook its rear rim (13). At the end of the injection stroke of the plunger (2), a rear head (8) of the stem (3) of the plunger (2) radially opens the retaining tongues (10) apart, which release thereby the needle-covering sleeve (14). Then, the latter is axially advanced by a spring (16), until it entirely covers the needle (5). The needle-carrier (4, 104) has at least one lateral locking projection (28), slidably engaging in a longitudinal slot (18), which is formed in the needle-covering sleeve (14) and is delimited at its sides, at least in its progressively tapering rear end (118), by two convergent and elastically openable stop sticks (19) which allow the passage of the locking projection (28) between their free ends, but then point against it and fasten it to the needle-covering sleeve.

18 Claims, 7 Drawing Sheets

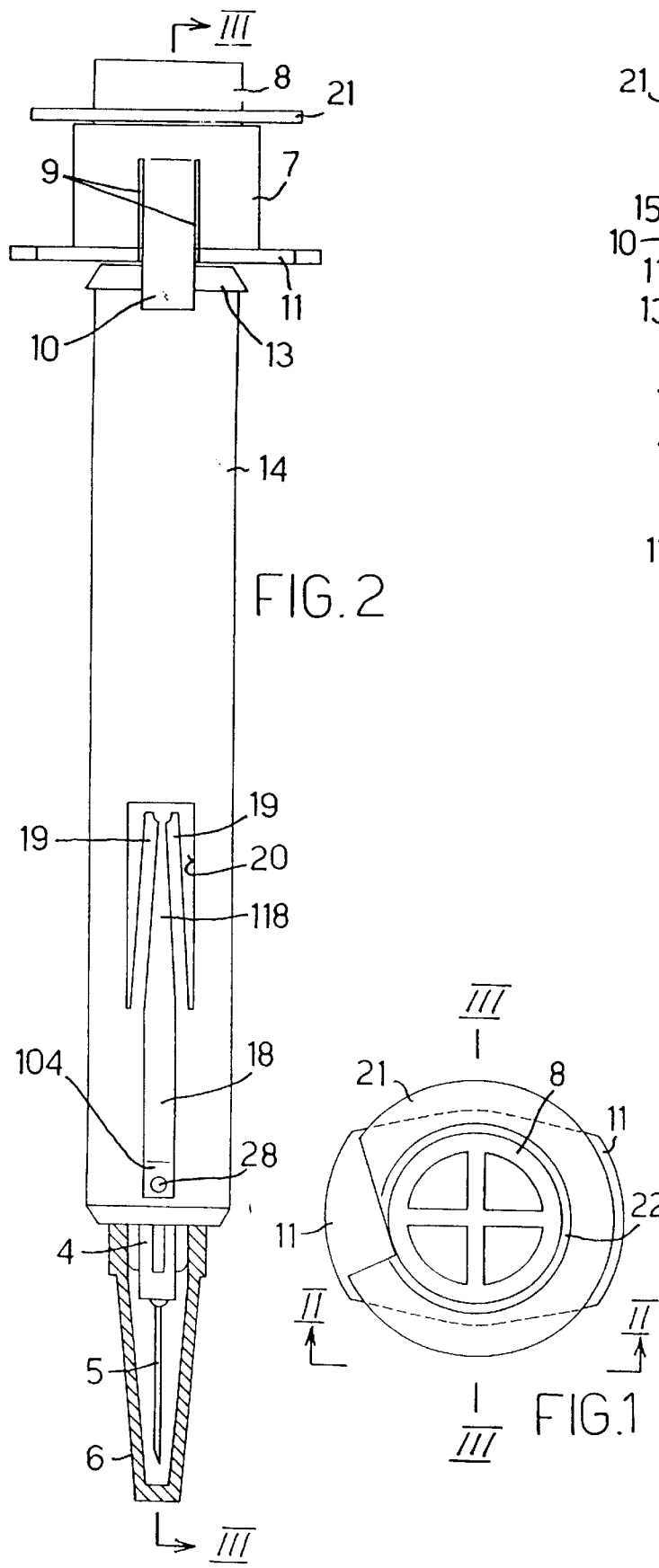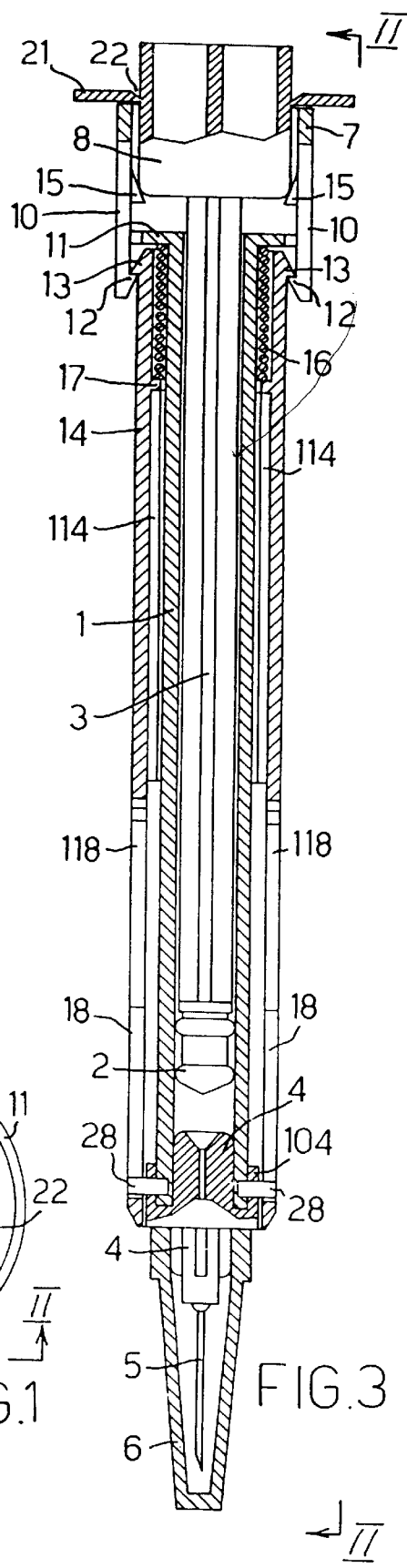

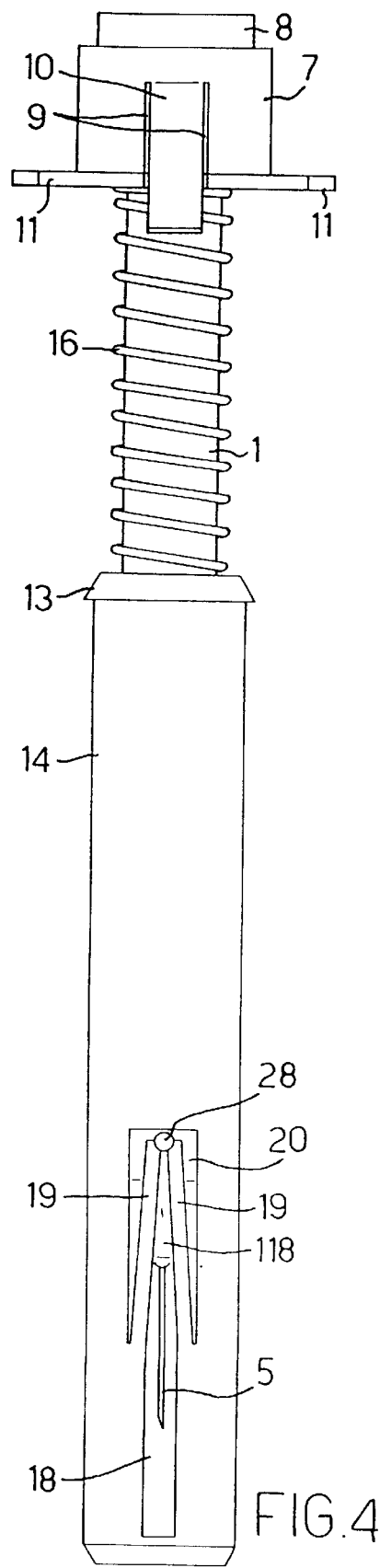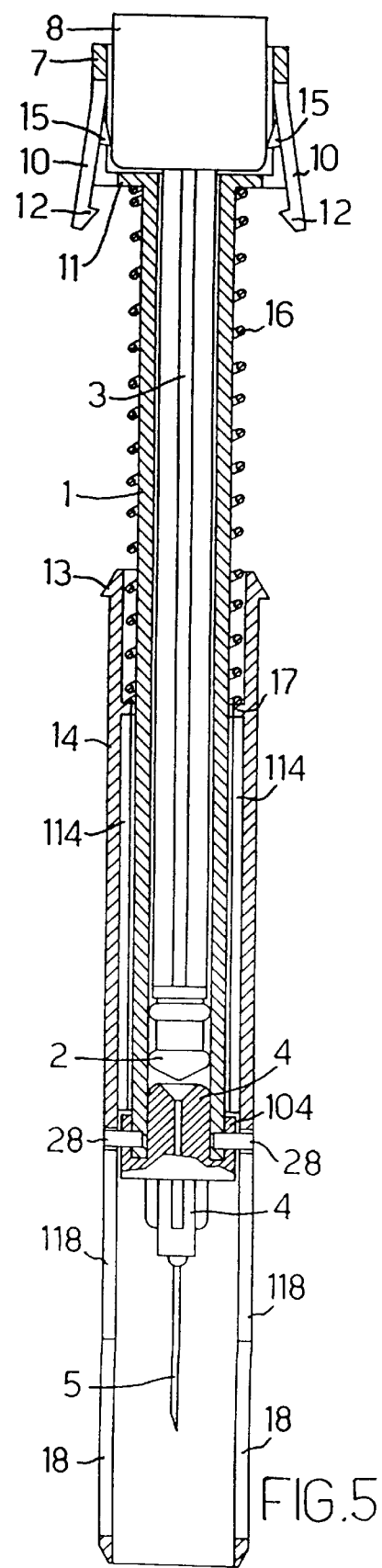
FIG.4
FIG.5

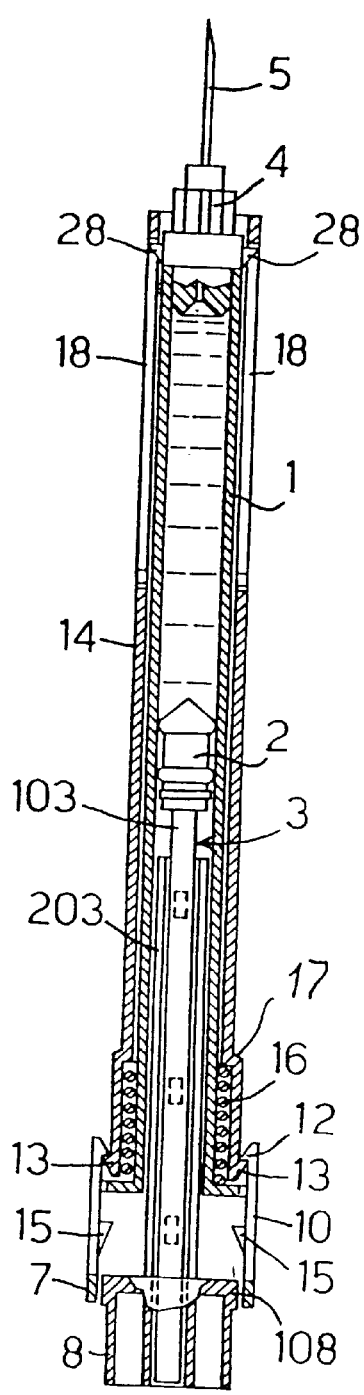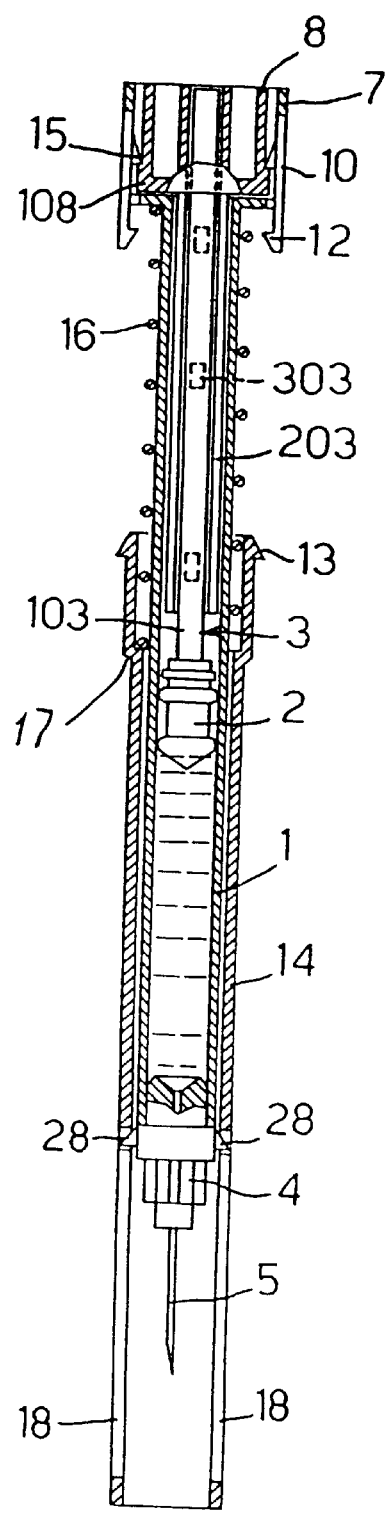
FIG. 13
FIG. 14

DISPOSABLE SAFETY SYRINGE

SUMMARY OF THE INVENTION

The present invention relates to a disposable safety syringe, comprising:
- a) a cylindrical syringe barrel;
- b) an injection needle, being integral with a needle-carrier, which is attached to the fore end of the syringe barrel;
- c) a plunger which is slidable in the syringe barrel and has an injection stroke which extends from a retracted utmost syringe-filling position, wherein the liquid medicine has been aspired, to a forwardmost position, and is fitted at its back with a manually drivable stem, driven out of the syringe barrel through the open rear end thereof;
- d) a needle-covering sleeve, which is axially fitted on the syringe barrel, so as to slide from a retracted rest position, in which it leaves the needle exposed, into an advanced safety position, in which it entirely covers the needle;
- e) plunger-clamping means, consisting of hook-like interacting means, which are provided at the rear side of the syringe barrel and at the rear side of the needle-covering sleeve, and are initially engaged with each other so as to retain the needle-covering sleeve in its retracted rest position, whereas they are automatically disengaged from each other by the plunger stem, in the last portion of the injection stroke of the plunger, thereby releasing the needle-covering sleeve;
- f) a spring, interposed between the rear of the syringe barrel and the needle-covering sleeve, which stresses the needle-covering sleeve, once it is released from the hook-like means, towards its advanced safety position, first by making it elastically adhere to the patient body, and then by progressively advancing it, on extracting the needle from the patient body, at the end of the injection, until it entirely covers the extracted needle.

The invention has the object to provide a disposable safety syringe of the type described hereinbefore, which has a simpler and cheaper construction and an easier and safer operation.

This object is achieved by the invention with a disposable safety syringe of the type described hereinbefore, in which:
- g) the needle-covering sleeve has a rear rim having the shape of an outwardly projecting hook-like tooth, cooperating with one or more complementary inwardly projecting hook-like teeth, provided on retaining tongues, which extend forwardly in the longitudinal direction of the syringe from a head located at the rear end of the syringe barrel and are automatically movable from a radially retracted hooking position, in which their teeth hook the rim of the needle-covering sleeve, holding it in its retracted rest position, into a radially opened out releasing position, in which their teeth are released from the rim of the needle-covering sleeve and disengage it;
- h) the rear end of the plunger stem is provided with means which cooperate with the retaining tongues and automatically cause these tongues to move from their radially retracted hooking position, into their radially opened out releasing position, at the end of the injection stroke of the plunger;
- i) the needle-carrier has at least one lateral locking projection, which projects radially outwards, and slidably engages in a longitudinal slot, formed in the needle-covering sleeve, whereas, at the rear end of said slot, there are provided automatic stop means, engaging said lateral locking projection, preventing any axial movement thereof with respect to the needle-covering sleeve, in the advanced safety position thereof, thus securing at least the needle-carrier to the needle-covering sleeve.

The syringe according to the invention is provided with an automatic needle coverage, the needle-covering sleeve, which is released from the plunger stem when the latter, at the end of the injection, reaches the end-of-stroke position, for injecting the medicine. Once the needle of the syringe has been extracted from the muscle or vein of the patient and, at the latest, once the pressure of the syringe-controlling fingers has been released, the needle-covering sleeve immediately and automatically covers the needle, locking it therein. Any attempt to remove the needle protection would cause it to be torn away from the syringe, therefore the needle would be well protected ad locked in its protective needle-covering shell.

A preferred embodiment of the syringe according to the invention is based on the acknowledgement that the needle-covering sleeve, which is only free to snap forwardly to its advanced safety position, when the syringe plunger has run the whole injection stroke, cannot prevent the syringe from being used for more than one user, by injecting each one with only a part of the total volume of liquid, aspirated by the syringe. Therefore, said embodiment of the invention is aimed at providing a disposable safety syringe which ensures the prevention of a shared use thereof, causing the needle-covering sleeve to snap forwardly to its needle-covering position, even when smaller doses of the maximum contents of the syringe are injected.

The invention achieves the above objects by providing a syringe according to claim 1, further having the following characteristics:
- k) the cooperating plunger-clamping means, provided at the rear end of the plunger stem and of the syringe barrel are arranged to fasten the plunger stem to the syringe barrel, so as to prevent it from being unlocked in either direction;
- l) the plunger stem and the syringe barrel are provided at their rear end with cooperating safety means, which are manually removable or disengageable, and initially (in the syringe supplied condition) prevent any forward movement of the plunger stem, retaining it in a rest or starting position, in which the plunger-clamping means, on the plunger stem and on the syringe barrel are disengaged from each other and from which position the plunger stem may be caused to run (once the safety means have been released) a terminal forward stroke, substantially corresponding to the minimum medicine dose which can be injected by the syringe, and thereafter the plunger-clamping means on the plunger stem and on the syringe barrel engage with each other and secure the plunger stem to the syringe barrel,
- m) the plunger stem has a length between
  - a maximum length, wherewith, in the initial rest position of the plunger stem, the fore end of the plunger is set back from the bottom of the syringe barrel, at a distance substantially corresponding to the above mentioned terminal forward stroke of the plunger stem, and the greatest quantity of medicine that can be injected by the syringe corresponds to the quantity drawn in, and
  - a minimum length, wherewith, in the initial rest position of the plunger stem, the fore end of the plunger is set back from the bottom of the syringe barrel, at a distance substantially corresponding to the longest possible further backward stroke of the plunger, from this position to the retracted utmost syringe-filling i.e. aspirating position and the greatest quantity of medicine that can be injected by the syringe substantially corresponds to the terminal forward stroke of the plunger stem (smallest injectable dose).

Advantageously, the syringe is associated to a package of liquid medicine, and the stem of its plunger has such a length that the maximum syringe-filling volume of medicine which can be aspirated is at the most equal to the volume of the medicine contained in the package or preferably smaller.

Syringes for injecting predetermined medicine doses, or smaller, may be provided with stems having a corresponding fixed length, and being by turns fitted in the syringe barrel during the syringe manufacturing process.

The stem may be advantageously provided with a variable length, for example with a telescopic adjustment.

The advantages of the present invention are apparent from the above description. By a single type of syringe, the problem related to the shared use of syringes may be obviated, particularly when the doses to be injected are smaller than the utmost filling dose. Particularly, when syringes are sold together with the medicine, the length of the plunger may be determined in such a way as to only allow a predetermined dose of medicine to be injected. The dose allowed to be injected before the plunger is clamped and the needle-covering sleeve snaps into the operating position, rendering the syringe unusable, may vary between a maximum dose, corresponding to the greatest volume of liquid that can be aspirated, and the smallest injectable dose, which corresponds to the volume defined by the terminal stroke of the plunger between the starting position and the position in which the plunger and the plunger-clamping means are mutually engaged. This injectable dose may be determined by simply providing plunger stems having correspondingly different lengths. The telescopic construction of the stem allows for the use of a single stem for all types of syringe, reducing manufacturing costs and limiting any possible increase thereof only to one additional part of stem.

Even though the syringe according to the invention requires the quantity of the aspirated medicine to be slightly greater than the injectable quantity, the costs involved by a certain limited quantity of non consumable medicine are not comparable to public health costs involved by people suffering from serious infections, the latter being much more burdensome to the community. This is especially remarkable in geographical areas in which public health is significantly supported by solidarity organizations, such as the World Health Organization, and others, since the small immediate higher expense for the unusable medicine is largely compensated by the savings obtained by limiting the infection rate due to the shared use of syringes.

These characteristics of the invention and others, as well as the advantages derived therefrom will appear more clearly from the following disclosure of certain preferred embodiments, illustrated not by way of restriction in the accompanying drawings, in which:

BRIEF DESCRIPTION OF THE DRAWINGS

FIG. 1 is an axial rear end view of a first embodiment of the disposable safety syringe according to the invention.

FIG. 2 is a lateral elevational view of the syringe, in the direction of arrows II—II in FIGS. 1 and 3, and in the initial condition.

FIG. 3 is an axial sectional view of the syringe, taken on lines III—III in FIGS. 1 and 2 and in the same initial condition.

FIGS. 4 and 5 show the syringe in a view corresponding to FIG. 2 and in a longitudinal sectional view corresponding to FIG. 3, but in the final condition, when the injection has been executed and the needle has been extracted from the patient body.

FIG. 13 is a view of the syringe as in FIGS. 11 and 12, when air has just been discharged therefrom.

FIG. 14 is a view of the syringe as in FIGS. 11 to 13, when a predetermined quantity of liquid, smaller than the drawn in quantity, has just been injected, with the plunger-clamping and needle-covering means in the operating condition.

DETAILED DESCRIPTION

Figure 6:
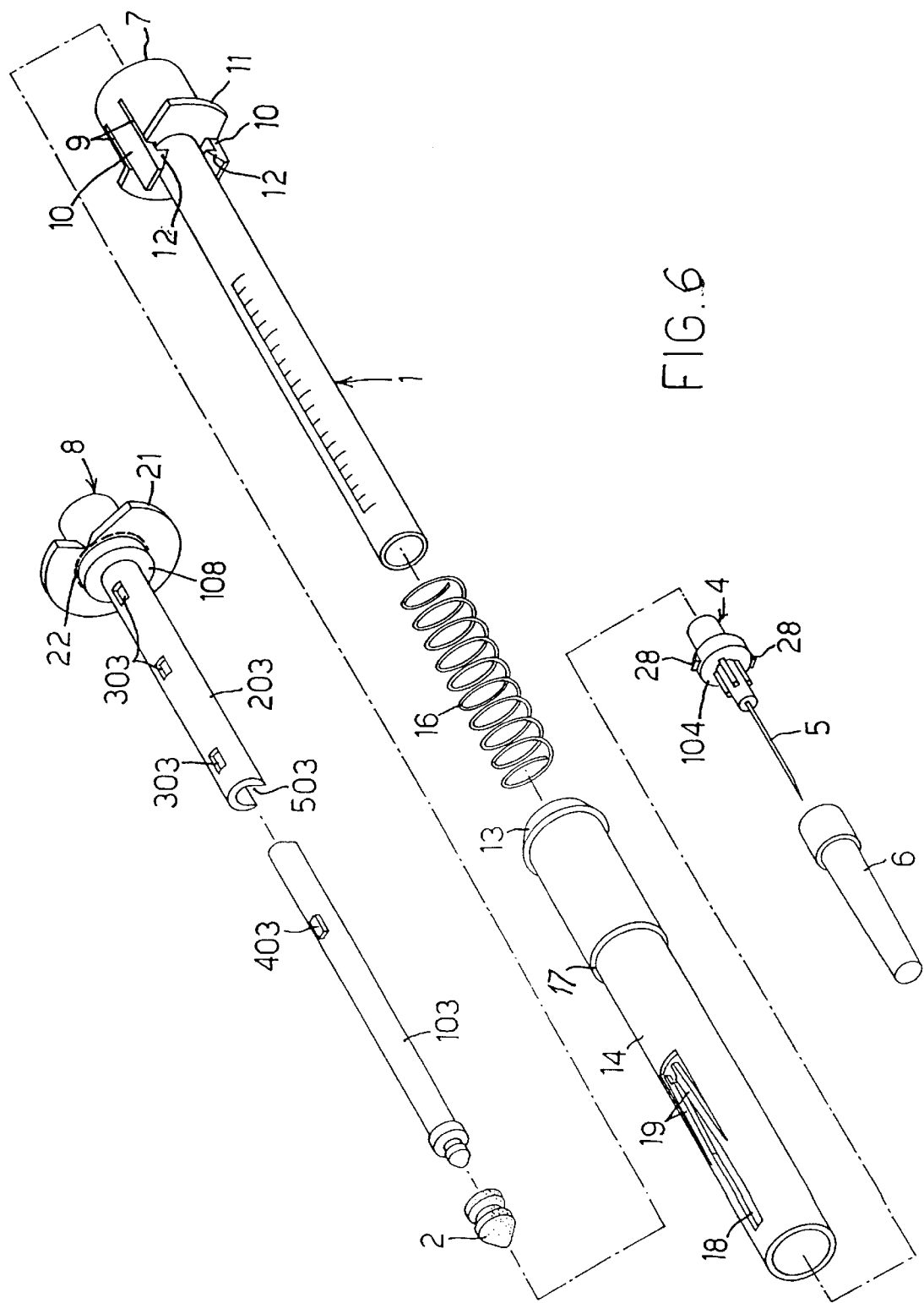
FIG. 6 is an exploded perspective view of a further embodiment of the syringe according to the present invention.

In the embodiment according to FIGS. 1 to 5, the disposable safety syringe according to the invention comprises a cylindrical barrel 1, in which a plunger 2 is slidable in a fluid-tight manner. The plunger 2 is attached to a stem 3, which extends axially in the syringe barrel 1 and is driven out of it, through its open rear end. At the fore end of the syringe barrel 1, a needle-carrying member 4 is attached in a fluid-tight manner, the injection needle 5 being fixed thereto. In the illustrated embodiment, the needle-carrier 4 is engaged in the fore end of the syringe barrel 1 like a plug, and has an outward flap 104 covering the fore end of the syringe barrel 1. The inner space of the syringe barrel 1 communicates with the tubular injection needle 5, through a hole formed in the needle-carrier 4. The needle 5 is initially protected by a cap 6, fitted on the needle-carrier 4.

The syringe barrel 1 is provided, at its rear end, with two radial diametrically opposite tabs 11, and a widened, hollow head 7 open at its back, wherein a head 8, provided at the rear end of the stem 3 of the plunger 2 may be inserted. In two diametrically opposite locations, two retaining tongues are formed on the sidewall of the head 7 of the syringe barrel 1, by means of cuts 9, and extend forwardly in the longitudinal direction beyond the fore edges of the head 7 and of the radial tabs 11 of the syringe barrel 1. At their free fore ends, the retaining tongues 10 have each one hook-like tooth 12, which is turned radially inwardly and cooperates with the rear rim, having the shape of a hook-like tooth 13, turned radially outwardly, of a needle-covering sleeve 14, which is slidably axially fitted on the syringe barrel 1. Normally, in the rest condition, the retaining tongues 10 lie in a radially retracted position, i.e. substantially parallel to the longitudinal axis of the syringe, and in which their hook-like teeth 12 are engaged with the rim, formed with a hook-like counter-tooth, of the needle-covering sleeve 14, as shown in FIG. 3. However, said retaining tongues 10 may be radially outwardly opened apart and brought to a position, in which their hook-like teeth 12 disengage from the rim, having the shape of a hook-like counter-tooth, of the needle-covering sleeve 14, as shown in FIG. 5.

In order to obtain said radial deflection of the retaining tongues, each retaining tongue 10 is provided—on its radial inner side—with a projection 15, protruding inside the hollow head 7 of the syringe barrel 1 and having a surface which is inclined in the rear-front direction towards the center axis of the syringe. These slanted inner projections 15 of the retaining tongues 10 cooperate with the fore rim (preferably rounded) and with the sidewall of the head 8 of the stem 3 of the plunger 2, as described hereafter.

For a certain length of its rear end part, the inside diameter of the needle-covering sleeve 14 is greater than the outside diameter of the syringe barrel 1, and the cylindrical hollow space resulting therefrom houses a helical spiral spring 16, which bears by its rear end against the radial tabs 11 of the syringe barrel 1 and against the bottom of the hollow head 7 of the syringe barrel 1, and by its fore end against an inward step 17 of the needle-covering sleeve 14. The rest of the needle-covering sleeve 14 may be as thick as the part thereof corresponding to the step 17 or may have angularly spaced longitudinal inner ribs 114, in such a way that it may be slidably guided on the outer wall of the syringe barrel 1.

At each of two diametrically opposite locations, the needle-carrier 4 has a lateral locking projection 28, which projects radially outwardly and is slidably engaged in an associated longitudinal slot 18 of the needle-covering sleeve 14. In the illustrated preferred embodiment, each locking projection 28 consists of a radial pin passing through the outward flap 104 of the needle-carrier 4 and engaging in a hole of the syringe barrel 1, thereby also advantageously anchoring mechanically the needle-carrier 4 to the syringe barrel 1. Nevertheless, each locking projection 28 may be made in any other manner, and may particularly be formed of one piece with the needle-carrier 4 or with its flap 104, without engaging the syringe barrel 1, and then the needle-carrier 4, 104 will be connected to the syringe barrel 1 by simply force-fitting and/or by gluing or welding.

Each longitudinal slot 18 formed in the needle-covering sleeve 14 has a fore part with a constant width, connected to a rear part 118, whose width progressively decreases towards the rear end of said needle-covering sleeve 14, and being delimited, at its sides, by two stop sticks 19 formed in the wall of the needle-covering sleeve 14 by providing an appropriately shaped aperture 20, on the needle-covering sleeve 14. The two stop sticks 19 converge towards the rear end of the needle-covering sleeve 14, each forming a progressively tapering length 118 of the slot. The rear free ends of the two stop sticks 19 are shaped so as to form each a housing for a locking projection 28 of the needle-carrier 4. In the rest position, the two convergent stop sticks 19 are touching, or almost touching each other with their rear free ends, but may be elastically opened apart, substantially in the tangential or circumferential direction with respect to the needle-covering sleeve 14 and to such an extent as to allow the passage of each locking projection 28 between their rear free ends, and beyond them, as described hereafter.

The above described disposable safety syringe operates as follows:

In the initial condition, i.e. the user-supplied condition, the different parts of the syringe are in the positions shown in FIGS. 2 and 3. More precisely, the needle-covering sleeve 14 is in a retracted rest position, in which it leaves the needle 5 exposed, and is held and hooked by the retaining tongues 10, which are set free and thus in their radially retracted position. The locking projections 28, formed of one piece with the needle-carrier 4, are in the fore end part of their respective slots 18 of the needle-covering sleeve 14. The helical spiral spring 16 is compressed and entirely housed in the rear part of the needle-covering sleeve 14, between the latter and the syringe barrel 1. The retaining tongues 10 are preferably as long as to hook and retain the needle-covering sleeve 14 in a retracted position, in which its rear rim is close to the head 7 of the syringe barrel 1, whereby the spring 16 is actually invisible. The plunger 2 and its stem 3 lie in an advanced position, in which the plunger 2 is close to the fore end of the syringe barrel 1, but is still able to run a small forward stroke. The rear head 8 of the stem 3 of the plunger 2 is partially inserted in the rear hollow head 7 of the syringe barrel 1, but is stopped in a position, in which it does not come into contact with the inner slanted projections 15 of the retaining tongues 10, or only touches said projections 15, without exerting any perceptible pressure thereon. In the illustrated embodiment, the head 8 is stopped by means of a safety flange 21, which extends all around the head 8 of the stem 3 of the plunger 2, for example covering slightly less than 360°, and bears against the rear edge of the hollow head 7 of the syringe barrel 1, thereby stopping the head 8 of the stem 3 of the plunger 2 in the above mentioned position, in which it does not interfere with the inner projections 15 of the retaining tongues 10.

The safety flange 21 is integral with the head 8 of the stem 3 of the plunger 2, through a circumferential weakened line 22 for predetermined breaking and easy tear-off operations, so as to be torn along said line 22 and manually removed before using the syringe. Naturally, the safety flange 21 may be replaced by any other tearable abutment member, similar or equivalent thereto, such as a collar, a ring, or one or more single radial projections.

Once the safety flange 21 is torn off and the protective cap 6 of the needle 5 is removed, the latter may be introduced, for example, in an ampoule containing the to-be-injected liquid, and this liquid may be aspirated in the syringe barrel 1, by pulling the plunger back, by means of the head 8 of the stem 3, and by bringing it to a retracted syringe-filling position. Naturally, the safety flange 21 may be torn off the head 8 of the stem 3 even after aspirating the liquid to be injected, i.e. after filling the syringe, and so said safety flange 21 may be also used to improve the seizure of the head 8 of the stem 3, to pull back the plunger 2.

The syringe being so filled, the injection is made in the usual way, since the needle-covering sleeve 14 is still hooked and held by the retaining tongues 10 in its retracted rest position, as shown in FIG. 3, in which it leaves the needle 5 exposed. In the final part of the injection stroke of the plunger 2, the head 8 of the stem 3, which now has no abutment by the safety flange 21, penetrates in the hollow head 7 of the syringe barrel 1 more deeply than before, for example up to the bottom of said head 7, or anyway to such an extent as to engage and push radially outwardly the inner projections 15 of the retaining tongues 10, and as to radially open, i.e. as to outwardly angularly deflect said retaining tongues 10, as shown in FIG. 5. While being opened apart, tie retaining tongues 10 release the needle-covering sleeve 14, which is pushed by the spring 16 and advanced on the syringe barrel 1 until it adheres with its fore end against the part of the patient body, in which the needle 5 is inserted. Then, while the needle 5 is extracted from the patient body, the needle-covering sleeve 14 is further advanced with respect to the syringe barrel 1 by the spring 16, until it reaches a final advanced safety position, in which besides entirely covering the needle 5, it also extends beyond the pointed end thereof, to such an extent as to prevent the needle to be accessed by a finger, as shown in FIGS. 4 and 5.

During the above described axial forward movement of the needle-covering sleeve 14, the lateral locking projections 28 of the needle-carrier 4, 104, slide at first in their respective slots 18 having uniform width and then in the slots 118, associated thereto, progressively narrowing between the convergent stop sticks 19, thereby elastically opening said sticks 19 apart. A short while before the plunger 2 reaches the end of its injection stroke and the stem 3 is stopped by the abutment of its head 8 against the bottom of the hollow head 7 of the syringe barrel 1, as shown in FIG. 5, the lateral projections 28 of the needle-carrier 4, 104 pass between the rear free ends of their respective stop sticks 19, and carry with them these ends of said stop sticks 19, which elastically close, i.e. approach again before the locking projections 28, and lock them to the needle-covering sleeve 14, as shown in FIG. 4. Particularly, each locking projection 28 is caught between the approached or joined free ends of their respective stop sticks 19 and the rear transverse edge of the shaped aperture 20. By this arrangement, the needle-covering sleeve 14 is fastened to the needle-carrier 4, 104 and—in the illustrated embodiment—also to the syringe barrel 1, in its advanced safety position, in which it entirely covers the needle 5 and prevents it from being accessed. In these conditions, any reuse of the syringe for another injection is impossible. The attempt to forcedly slip axially the needle-covering sleeve 14 either forward or backward would cause the fore end of the syringe barrel 1 and/or the needle-carrier 4, 104 to break, or—when the lateral locking projections 28 are only integral with the needle-carrier 4, 104—would cause not only the needle-covering sleeve 14, but also the needle-carrier 4, with the needle 5, to be torn off and removed, with the needle being anyway inaccessibly held inside the needle-covering sleeve 14 and being linked thereto.

The embodiment of the syringe illustrated in FIGS. 6 to 14 mostly corresponds to that according to FIGS. 1 to 5. Like or equivalent parts are designated by the same reference numerals, the above description with reference to FIGS. 1 to 5 being applicable, as regards construction and operation. The differences between the embodiment of FIGS. 6 to 14, and the embodiment of FIGS. 1 to 5 will be only described hereafter.

Particularly, in the embodiment according to FIGS. 6 to 14, the head 8 of the stem 3 has a peripheral annular extension 108, on the side connecting it to the stem 3, having a predetermined axial thickness and being adapted to form an outward annular shoulder. The latter is meant to cooperate with the projections 15 for deflecting the retaining tongues 10 of the sleeve 14, both for causing them to be opened out, when the sleeve 14 is in the disengaged position, and for engaging the rear part of the peripheral annular shoulder 108 of the stem head 8, which is locked and cannot move neither backward nor forward between the projections 15 and the rear widened end of the syringe barrel 1. Hence, the tongues 10 are used as means for retaining the sleeve 14 during the injection, and the plunger in its utmost penetration position inside the syringe barrel 1.

Moreover, according to a further characteristic, the plunger stem 3 is made to be substantially telescopically extensible, there being provided means for fixing the different length adjustments of the stem 3.

With particular reference to FIGS. 6 to 10, the stem has a circular cross section and is composed of two parts, which are axially movable, relative to each other. The two parts 103 and 203 have cooperating radial means 303, 403, for locking the two parts 103, 203 in the selected position. Advantageously, one stem part 103 has a longitudinal groove 503, which provides it with a U-shaped cross section, and is the engagement seat for the other stem part 203, having a complementary shape, and such as to complete the cross section of the part 103, forming therewith a complete circular section. At the bottom of the engagement seat on the side opposite to the open side, the part 103 has regularly and predeterminedly spaced notches or apertures 303, whereas on the side associated thereto, the second stem part 203 has complementary teeth 403.

Thanks to the above expedients, it is possible to select, during manufacture, the desired length of the stem 3, by varying the relative position of the two stem parts 103, 203. The complementary non round shape of the housing groove 503 and of the stem part 203 is such as to prevent mutual rotation thereof. The notches or apertures 303 and the projections 403 allow the two stem parts 103, 203 to be fixed with respect to a mutual axial movement thereof, whereas the mutual engagement of the two parts 103, 203 is remarkably simple. The projections 403 and the total diameter of the stem 3 have such radial dimensions, possibly by also making use of axial guide ribs, that when the stem 3 is fitted in the syringe barrel 1, the two stem parts 103, 203 are stably linked to each other, any dimensional tolerances required to allow the stem 3 to slide being also considered.

The inside diameter of the needle-covering sleeve 14 is, for a certain length of the rear end portion thereof, greater than the outside diameter of the syringe barrel 1, and the cylindrical hollow space resulting therefrom houses the helical spiral spring 16, which bears by its rear end against the radial tabs 11 of the syringe barrel 1 and against the bottom of the hollow head 7 of the syringe barrel 1, and by its fore end against an inward step 17 of the needle-covering sleeve 14. The rest of the needle-covering sleeve 14 may be as thick as the part thereof corresponding to the step 17 or may have angularly spaced longitudinal inner ribs 114, in such a way that it may be slidably guided on the outer wall of the syringe barrel 1.

In the embodiment according to FIGS. 6 to 14, while the sleeve 14 snaps forwards, the head 8 of the stem 3 advances to the position in which it hooks the outward peripheral annular shoulder 108 by the teeth 15 and the head 8, the stem 3 and the plunger 2 are kept locked so that they cannot move in either longitudinal direction of the syringe barrel 1.

Figure 8:
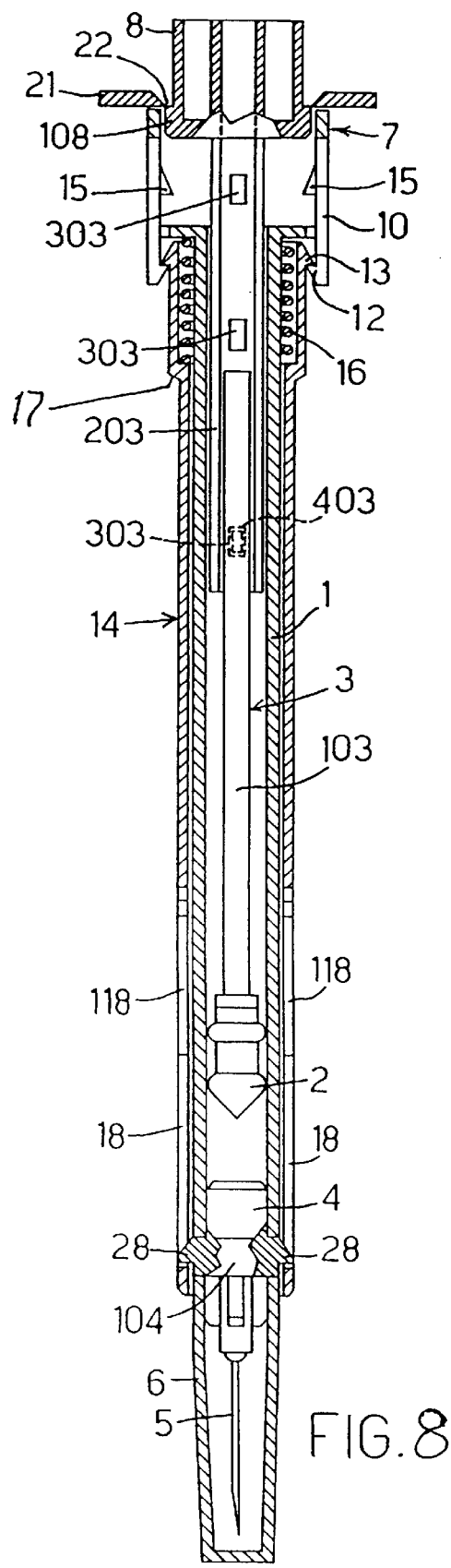
FIG. 8 is an axial sectional view of the syringe according to FIG. 7, having the longest possible stem.
Figures 9, 10:
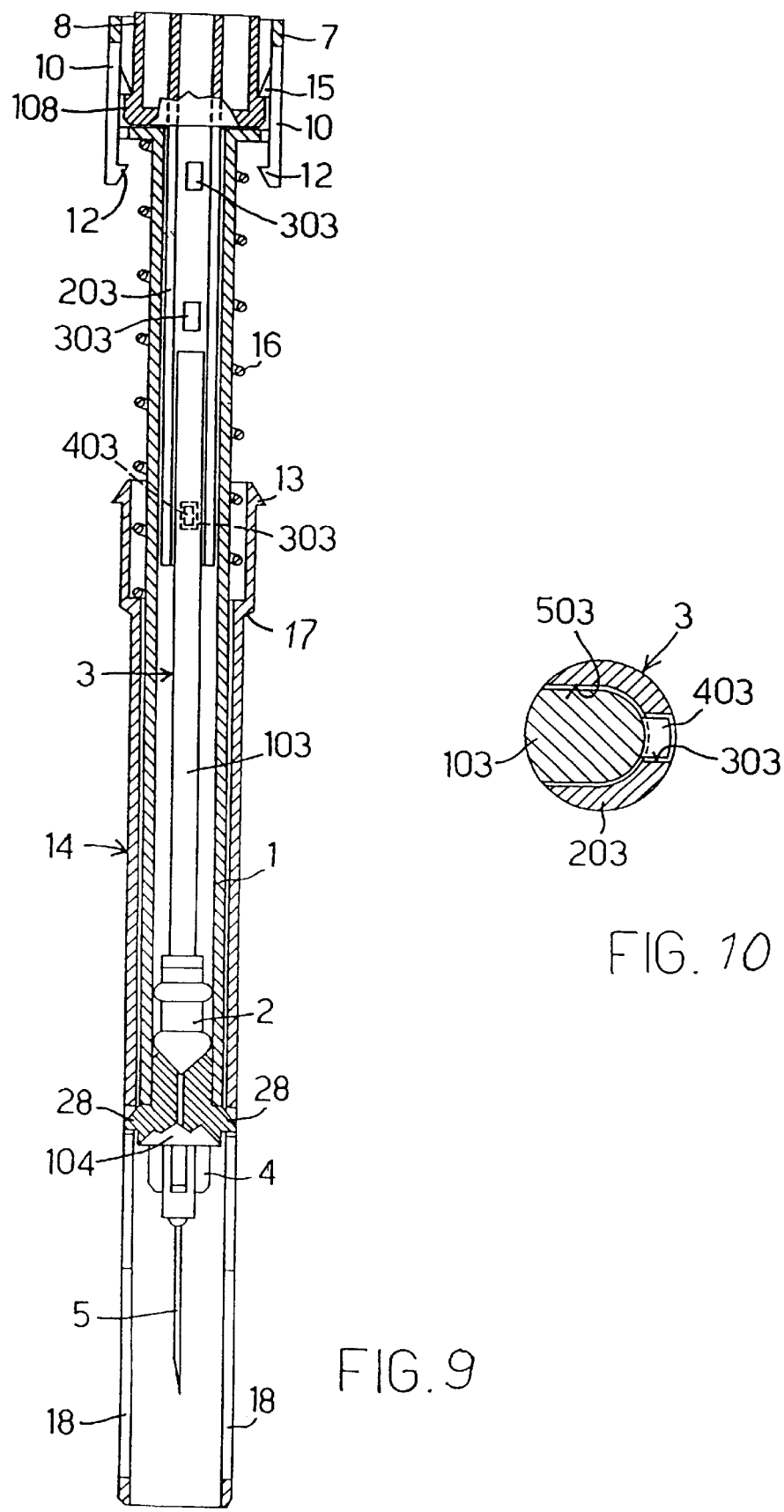
FIG. 9 is an axial sectional view of the syringe according to FIG. 8, with the plunger being in the end-of-stroke condition.
FIG. 10 is a cross sectional view of the telescopically extensible stem.
Figure 11:
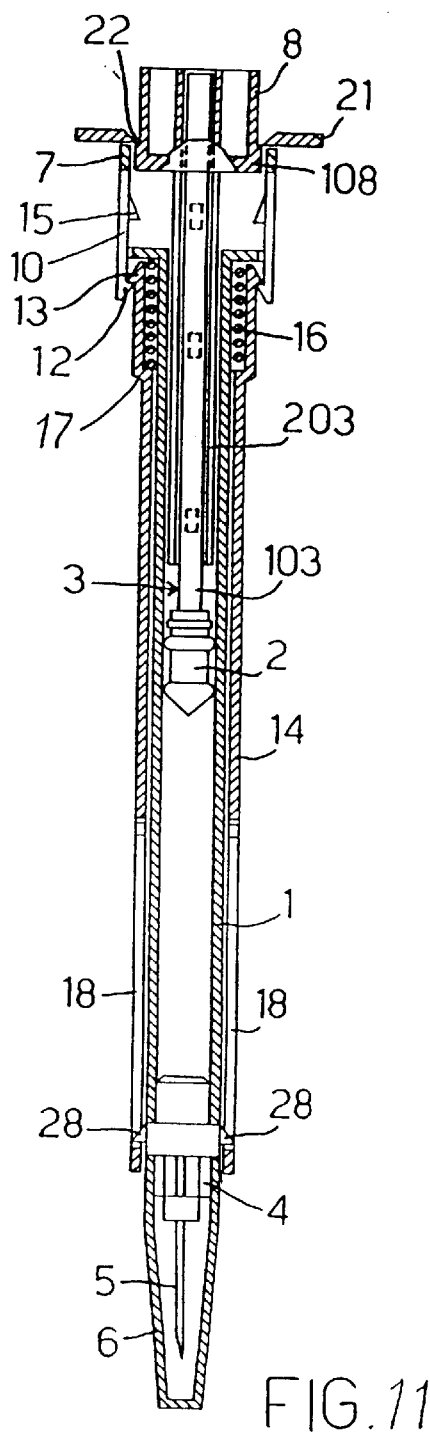
FIG. 11 is a view of the syringe according to the invention as in FIG. 8, in the version with the shortest possible stem, and with operating safety means.
Figure 12:
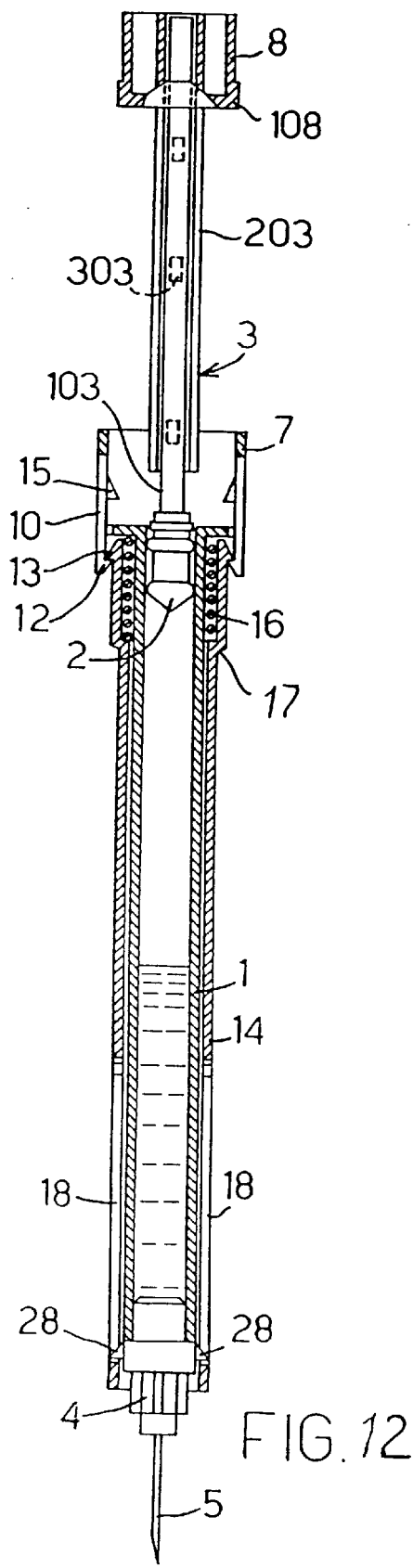
FIG. 12 is a view of the syringe as in FIG. 11, when the liquid to be injected has just been aspirated.

When the stem 3 is substantially as long as the syringe barrel, or anyway adapted thereto, the greatest possible quantity of to-be-injected liquid can be aspirated. In this case, as shown in FIGS. 8 and 9, before disengaging the sleeve 14 and bringing the plunger 2, i.e. the stem 3 into the position in which they are secured to the syringe barrel 1, the whole volume of liquid aspirated by the syringe is to be injected. As previously explained, when the injection of smaller doses with respect to the greatest quantity of liquid which may be aspirated by the syringe is sufficient, this configuration according to FIGS. 8 and 9 does not ensure an unshared use thereof.

Therefore, the configuration illustrated in FIGS. 8 and 9, is intended to be used when a single person, or any other patient must be injected with the whole maximum volume of liquid which may be aspirated.

In order to obtain a disposable syringe even when the dose to be injected is smaller than the maximum volume that can be aspirated, the length of the stem 3 must only be shortened.

So, in the starting position, the plunger 2 will be in a backward intermediate position in the syringe barrel 1. The whole must be dimensioned so that the suction stroke allows to draw in a quantity of liquid being greater than the quantity to be injected, whereas, once a quantity of air corresponding to the initial volume between the plunger 4 in the starting position and the head of the syringe barrel 1 is discharged, it is possible to inject a dose of liquid being smaller than the quantity drawn in. Thanks to the shortening operation, the head 8 of the stem 3 can cooperate with the retaining tongues 10 before the whole drawn liquid is injected, and after the predetermined dose is injected.

This operation is shown in FIGS. 11 to 14. These figures illustrate the extreme case, opposite to that of FIGS. 7 to 9. In FIGS. 11 to 14, the stem 3 has the minimum possible length. This length is such that, after the liquid having been aspirated (FIG. 12) and air having been discharged (FIG. 13), the possible injection stroke with that syringe corresponds to the smallest injectable dose, i.e. substantially to the axial length of the hollow head 7 of the syringe barrel 1.

Figure 7:
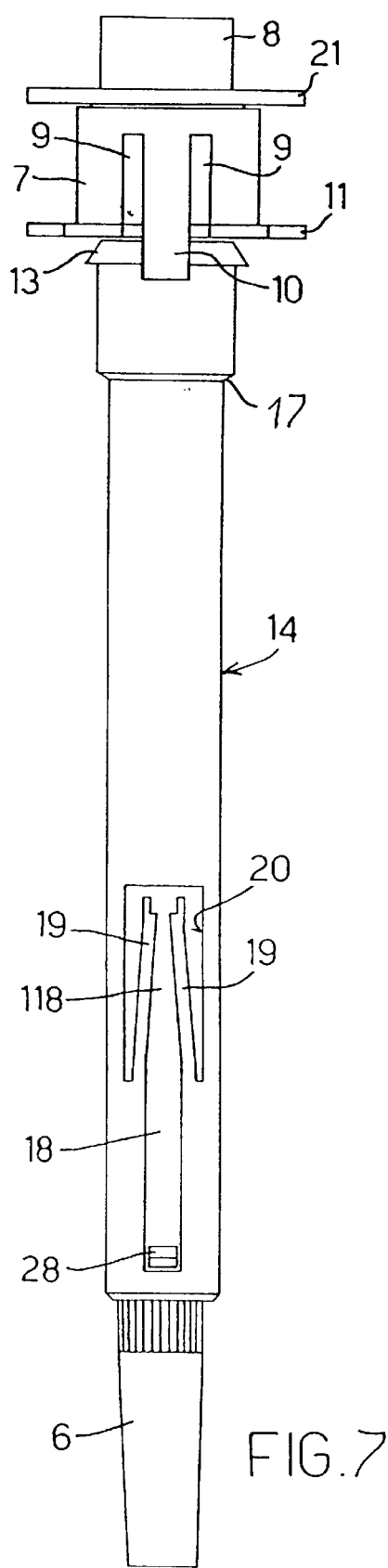
FIG. 7 is a lateral elevational view of the syringe according to FIG. 6, in the assembled condition and with operating safety means.

If the length of the stem 3 is intermediate between the maximum as in FIGS. 7 to 9, and the minimum, as in FIGS. 11 to 14, the injectable dose may be varied as needed.

In any case, the dose predetermined by selecting the length of the stem will only and exclusively be injectable, since when the predetermined dose has been injected, the means for releasing the sleeve 14 and the plunger-clamping means will be unpreventably operated.

What is claimed is:

1. A disposable safety syringe, comprising:
   a) a cylindrical syringe barrel;
   b) an injection needle integral with a needle-carrier attached to a fore end of the syringe barrel;
   c) a plunger slidable in the syringe barrel, an injection stroke on the plunger extending from a retracted maximum syringe-filling position, liquid medicine aspired to a forwardmost position, and a manually drivable stem fitted on a rear of the plunger extending through the open rear end of the syringe barrel thereof;
   d) a needle-covering sleeve axially fitted on the syringe barrel slidable from a retracted rest position for leaving the needle exposed to an advanced safety position for entirely covering the needle;
   e) plunger-clamping means, consisting of hook-like interacting means provided at the rear of the syringe barrel, the clamping means being initially engaged with the needle-covering sleeve for retaining the needle-covering sleeve in the retracted rest position, the stem on the plunger automatically disengaging the clamping means in an end portion of the injection stroke of the plunger thereby releasing the needle-covering sleeve;
   f) a spring releasably attached to the interacting means and interposed between the rear of the syringe barrel and the needle-covering sleeve for moving the needle-covering sleeve towards the advanced safety position, the needle-covering sleeve adapted for elastically adhering to a patient body, and then progressively advancing even after extracting the needle from the patient body after injection of the medicine until the needle is entirely covered by the needle covering sleeve;
   g) the needle-covering sleeve further comprises a rear rim shaped as an outwardly projecting hook-like tooth and cooperating with at least one complementary inwardly projecting hook-like tooth provided on retaining tongues, the teeth extending forwardly in a longitudinal direction of the syringe from a head at the rear end of the syringe barrel, wherein the teeth are automatically movable from a radially retracted hooking position, when the teeth hook the rim of the needle-covering sleeve for holding the sleeve in the retracted rest position, to a radially opened out releasing position, in which the teeth are released from the rim of the needle-covering sleeve for disengaging the sleeve;
   h) a rear end of the stem having cooperating means which cooperate with the retaining tongues and automatically cause the tongues to move from radially retracted hooking positions to radially opened out releasing positions when the injection stroke of the plunger ends;
   i) the needle-carrier having at least one lateral locking projection projecting radially outwards and slidably engaging in a longitudinal slot in the needle-covering sleeve, automatic stop means on a rear end of the slot engaging the lateral locking projection for preventing any axial movement thereof with respect to the needle-covering sleeve in the advanced safety position thereof, thus securing at least the needle-carrier to the needle-covering sleeve.

2. The syringe of claim 1, wherein the head on the rear end of the syringe barrel is hollow and open at a back side forming a hollow head, and the retaining tongues are formed on walls of the hollow head as cuts with projections on inner sides and protruding inside the hollow head for cooperating with the head on the rear end of the stem and penetrating the hollow head of the syringe barrel, wherein the hollow head remains in an initial idle position locked by removable safety means without acting on the inward projections of the retaining tongues lying in the radially retracted hooking position, and wherein the hollow head is in a forward operating position after removal of the safety means thereby pushing the inward projections of the retaining tongues outwards and moving the tongues into the radially opened-out releasing position.

3. The syringe of claim 1, wherein the removable safety means locking the head on the rear end of the stem of the plunger in the initial idle position consists of at least one projection extending around the head of the stem on at least one portion of a perimeter, and cooperating, as an abutment member, with a rear edge of the rear hollow head of the syringe barrel and wherein the projection is connected to the head of the stem by means of a weakened, predetermined easy tear-off line.

4. The syringe of claim 3, wherein the spring is a helical spiral spring housed in a hollow space formed between the rear of the needle-covering sleeve and the syringe barrel, bearing on one end against a bottom of the hollow head of the syringe barrel and/or against radial rear tabs of the syringe barrel and bearing on another end against an inward step of the needle-covering sleeve.

5. The syringe of claim 4, wherein when the needle-covering sleeve is in the retracted rest position, the rear rim of the needle-covering sleeve is close to the radial tabs at the rear end of the syringe barrel and/or close to the rear head of the syringe barrel.

6. The syringe of claim 1, wherein the locking projection is unitarily formed with the needle-carrier.

7. The syringe of claim 1, wherein the locking projection is connected to the needle-carrier.

8. The syringe of claim 1, wherein the locking projection is fastened to the needle-carrier and to a corresponding fore part of the syringe barrel.

9. The syringe of claim 8, wherein the needle-carrier is engaged in the fore end of the syringe barrel and has a flap covering the fore end of the syringe barrel, wherein the locking projection consists of a radial pin, passing through the flap of the needle-carrier and engaging in a radial hole of the syringe barrel.

10. The syringe of claim 1, wherein the longitudinal slot has a progressive taper at least in a rear portion towards the rear end of the needle-covering sleeve and two stop sticks for delimiting the taper on sides, wherein the two stop sticks converge until rear free ends of the sticks are almost in contact, the sticks being formed on the wall of the needle-covering sleeve by means of a shaped aperture and being elastically openable in tangential or circumferential direction to the needle-covering sleeve, wherein the two stop sticks are opened apart by the locking projection associated thereto when the needle-covering sleeve is being moved towards the advanced safety position, allowing the passage of the locking projection between the free ends when the needle-covering sleeve has almost reached the advanced safety position, and closing before the locking projection and pointing against the locking projection by the contacting free ends, when the needle-covering sleeve has reached the advanced safety position.

11. The syringe of claim 10, wherein when the needle-covering sleeve is in the advanced safety position each locking projection is embedded between the rear free joined ends of the convergent stop sticks, and a transverse edge, opposite to the shaped aperture formed in the needle-covering sleeve.

12. The syringe of claim 1, wherein k) the cooperating plunger-clamping means on the rear end of the stem and the syringe barrel are arranged to fasten the plunger stem to the syringe barrel for preventing the stem from being unlocked in either longitudinal direction;

l) the stem of the plunger and the syringe barrel are provided at the rear ends with cooperating safety means which are manually removable or disengageable, and in a syringe supply condition prevent any forward movement of the stem of the plunger by retaining the stem in a rest or starting position, and wherein the plunger-clamping means on the stem of the plunger and on the syringe barrel are disengaged from each other for allowing the stem to move in a terminal forward stroke, substantially corresponding to the minimum medicine dose injectable by the syringe, and thereafter the plunger-clamping means on the stem of the plunger and on the syringe barrel engage with each other and secure the stem of the plunger to the syringe barrel;

m) the stem of the plunger has a length between:

a maximum length that in the initial rest position of the stem of the plunger allows for the fore end of the plunger to be set back from a bottom of the syringe barrel at a distance substantially corresponding to the terminal forward stroke of the stem of the plunger, and wherein a greatest quantity of medicine injectable by the syringe corresponds to the quantity drawn in, and a minimum length that in the initial rest position of the stem of the plunger allows for the fore end of the plunger to be set back from the bottom of the syringe barrel at a distance substantially corresponding to a longest possible further backward stroke of the plunger to the retracted utmost syringe-filling or aspirating position and wherein the greatest quantity of medicine injectable by the syringe substantially corresponds to the terminal forward stroke of the stem of the plunger or smallest injectable dose.

13. The syringe of claim 12, wherein the stem has a length corresponding to a maximum syringe-filling volume of medicine aspirated which is almost equal to or lesser than a volume of the medicine in the package.

14. The syringe of claim 13, wherein plural syringes for injecting predetermined medicine doses have different stems having different corresponding fixed lengths, and being by turns fitted in the syringe barrel during a syringe manufacturing process.

15. The syringe of claim 14, wherein the stem has means for telescopic adjustment to form variable lengths with means for selecting and locking the stem at a desired length position.

16. The syringe of claim 15, wherein the safety means between the stem of the plunger and the syringe barrel consists of axial rear abutment extensions associated with the stem or to the syringe barrel, the axial abutment extensions cooperating with a radial expansion having a shape of a removable tear-away flange, the flange being attached to the syringe barrel or to the rear end of the stem of the plunger, the axial abutment extensions extending radially beyond maximum radial dimensions of the stem of the plunger or of the syringe barrel, the removable radial flange having a radial extension at least equal to or slightly greater than a radial position of the axial abutment extensions and being connected to the stem or to the syringe body by means of a weakened line, and wherein flange means are provided for seizing and tearing the flange away.

17. The syringe of claim 16, wherein the head at the rear end of the syringe barrel is a widened hollow head with at least one peripheral radially inwardly protruding teeth, the head of the stem being a complementary widened terminal head with at least two radially outward peripheral projections provided as a peripheral outward annular shoulder for cooperating with the tooth/teeth by engaging therewith on a rear part of the stem, through elastic overstress, wherein at a predetermined distance from the outward annular shoulder the widened head of the stem bears along the connection weakened line an outer radial annular flange for cooperating with a rear end edge of the hollow head of the syringe barrel and which extends over less than 360°.

18. The syringe of claim 17, wherein the hollow head on the rear end of the plunger stem has an outward annular shoulder with a rear part for engaging with projections after being released by the needle-covering sleeve release and wherein the shoulder is kept fastened to the syringe barrel in a longitudinally unmovable position in either direction.

* * * * *